(12) United States Patent
Barry et al.

(10) Patent No.: US 11,129,673 B2
(45) Date of Patent: Sep. 28, 2021

(54) EXTRA-AIRWAY VAPOR ABLATION FOR TREATING AIRWAY CONSTRICTION IN PATIENTS WITH ASTHMA AND COPD

(71) Applicant: Uptake Medical Technology Inc., Seattle, WA (US)

(72) Inventors: Robert Barry, Seattle, WA (US); Erik Henne, Seattle, WA (US)

(73) Assignee: Uptake Medical Technology Inc., Seattle, WA (US)

( * ) Notice: Subject to any disclaimer, the term of this patent is extended or adjusted under 35 U.S.C. 154(b) by 317 days.

(21) Appl. No.: 15/967,743

(22) Filed: May 1, 2018

(65) Prior Publication Data

US 2018/0318002 A1 Nov. 8, 2018

Related U.S. Application Data

(60) Provisional application No. 62/502,050, filed on May 5, 2017.

(51) Int. Cl.
*A61B 18/14* (2006.01)
*A61B 18/04* (2006.01)
(Continued)

(52) U.S. Cl.
CPC .......... *A61B 18/1492* (2013.01); *A61B 18/04* (2013.01); *A61B 5/389* (2021.01);
(Continued)

(58) Field of Classification Search
CPC .......... A61B 2017/00809; A61B 2018/00011; A61B 2018/00017; A61B 2018/00404;
(Continued)

(56) References Cited

U.S. PATENT DOCUMENTS 408,899 A 8/1889 Small
1,719,750 A 7/1929 Bridge
(Continued)

FOREIGN PATENT DOCUMENTS

AU 721086 B2 6/2000
EP 1003582 2/2003
(Continued)

OTHER PUBLICATIONS

Becker, et al.; Lung volumes before and after lung volume reduction surgery; Am J Respir Crit Care Med; vol. 157; pp. 1593-1599; (1998) Oct. 28, 1997.
(Continued)

*Primary Examiner* — Ronald Hupczey, Jr.
*Assistant Examiner* — Bradford C. Blaise
(74) *Attorney, Agent, or Firm* — Richard Batt

(57) ABSTRACT

A vapor-based ablation method mitigates constriction of the airways for the treatment of asthma and COPD. A vapor ablation catheter is advanced along the airways, through the airway wall, and to an extra-airway target tissue. The position of the catheter is assessed to determine whether the catheter is in contact with the target tissue. In embodiments, the distal energy delivery section of the catheter is manipulated to contact an exterior surface of the target tissue, or to enter the target tissue. Once the position is confirmed, vapor is delivered to the target tissue through an egress port with a sufficient amount of energy to ablate the target tissue. The target tissue may vary and include smooth muscle surrounding the airways, and nerves that control the smooth muscle. Methods for treating lung cancer are also described including delivering a vapor at lung tumors and growths, and blood vessels feeding the lung tumors and growths.

19 Claims, 9 Drawing Sheets

(51) Int. Cl.
*A61B 90/00* (2016.01)
*A61B 18/00* (2006.01)
*A61B 17/00* (2006.01)
*A61B 34/10* (2016.01)
*A61B 34/20* (2016.01)
*A61B 5/389* (2021.01)

(52) U.S. Cl.
CPC ..... *A61B 90/37* (2016.02); *A61B 2017/00809* (2013.01); *A61B 2018/00017* (2013.01); *A61B 2018/00404* (2013.01); *A61B 2018/00541* (2013.01); *A61B 2018/00577* (2013.01); *A61B 2018/00702* (2013.01); *A61B 2018/00714* (2013.01); *A61B 2018/00744* (2013.01); *A61B 2018/00791* (2013.01); *A61B 2018/00839* (2013.01); *A61B 2018/00982* (2013.01); *A61B 2018/048* (2013.01); *A61B 2034/107* (2016.02); *A61B 2034/2051* (2016.02); *A61B 2090/376* (2016.02); *A61B 2090/378* (2016.02)

(58) Field of Classification Search
CPC ........... A61B 2018/00541; A61B 2018/00577; A61B 2018/00982; A61B 2018/046; A61B 2018/048; A61B 18/1477; A61B 18/1492; A61B 2034/107; A61B 2034/2046; A61B 2034/2051; A61B 90/37; A61B 2090/376; A61B 2090/378
See application file for complete search history.

(56) References Cited

U.S. PATENT DOCUMENTS

| | | |
|---|---|---|
| 3,507,283 A | 4/1970 | Thomas, Jr. |
| 3,880,168 A | 4/1975 | Berman |
| 4,026,285 A | 5/1977 | Jackson |
| 4,713,060 A | 12/1987 | Riuli |
| 4,713,460 A | 12/1987 | Riuli |
| 4,773,410 A | 9/1988 | Blackmer |
| 4,793,352 A | 12/1988 | Eichenlaub |
| 4,915,113 A | 4/1990 | Holman |
| 4,950,266 A | 8/1990 | Sinofsky |
| 5,006,119 A | 4/1991 | Acker |
| 5,011,566 A | 4/1991 | Hoffman |
| 5,084,043 A | 1/1992 | Hertzmann |
| 5,112,328 A | 5/1992 | Taboada |
| 5,158,536 A | 10/1992 | Sekins |
| 5,263,951 A | 11/1993 | Spears |
| 5,331,947 A | 7/1994 | Shtuman |
| 5,334,190 A | 8/1994 | Seiler |
| 5,348,551 A | 9/1994 | Spears |
| 5,352,512 A | 10/1994 | Hoffman |
| 5,424,620 A | 6/1995 | Cheon |
| 5,462,521 A | 10/1995 | Brucker |
| 5,500,012 A | 3/1996 | Brucker |
| 5,503,638 A | 4/1996 | Cooper |
| 5,524,620 A | 6/1996 | Rosenschein |
| 5,529,076 A | 6/1996 | Schachar |
| 5,549,628 A | 8/1996 | Cooper |
| 5,562,608 A | 10/1996 | Sekins |
| 5,575,803 A | 11/1996 | Cooper |
| 5,591,157 A | 1/1997 | Hennings |
| 5,620,440 A | 4/1997 | Heckele |
| 5,695,507 A | 12/1997 | Auth |
| 5,735,811 A | 4/1998 | Brisken |
| 5,752,965 A | 5/1998 | Francis |
| 5,755,753 A | 5/1998 | Knowlton |
| 5,782,914 A | 7/1998 | Schankereli |
| 5,800,482 A | 9/1998 | Pomeranz |
| 5,824,703 A | 10/1998 | Clark |
| 5,827,268 A | 10/1998 | Lauger |
| 5,913,856 A | 6/1999 | Chia |
| 5,957,919 A | 9/1999 | Laufer |
| 5,964,752 A | 10/1999 | Stone |
| 5,972,026 A | 10/1999 | Laufer |
| 5,986,662 A | 11/1999 | Argiro |
| 5,989,445 A | 11/1999 | Wise |
| 6,032,077 A | 2/2000 | Pomeranz |
| 6,053,909 A | 4/2000 | Shadduck |
| 6,059,011 A | 5/2000 | Giolo |
| 6,083,255 A | 7/2000 | Laufer |
| 6,099,251 A | 8/2000 | LaFleur |
| 6,102,037 A | 8/2000 | Koch |
| 6,113,722 A | 9/2000 | Hoffman |
| 6,130,671 A | 10/2000 | Argiro |
| 6,131,570 A | 10/2000 | Schuster |
| 6,139,571 A | 10/2000 | Fuller |
| 6,156,036 A | 12/2000 | Sussman |
| 6,162,232 A | 12/2000 | Shadduck |
| 6,179,805 B1 | 1/2001 | Sussman |
| 6,194,066 B1 | 2/2001 | Hoffman |
| 6,200,333 B1 | 3/2001 | Laufer |
| 6,210,404 B1 | 4/2001 | Shadduck |
| 6,219,059 B1 | 4/2001 | Argiro |
| 6,273,907 B1 | 8/2001 | Laufer |
| 6,283,988 B1 | 9/2001 | Laufer |
| 6,283,989 B1 | 9/2001 | Laufer et al. |
| 6,299,633 B1 | 10/2001 | Laufer |
| 6,300,150 B1 | 10/2001 | Venkatasubramanian |
| 6,312,474 B1 | 11/2001 | Francis |
| 6,327,505 B1 | 12/2001 | Medhkour |
| 6,394,949 B1 | 5/2002 | Crowley |
| 6,398,759 B1 | 6/2002 | Sussman |
| 6,398,775 B1 | 6/2002 | Perkins |
| 6,409,723 B1 | 6/2002 | Edwards |
| 6,411,852 B1 | 6/2002 | Danek et al. |
| 6,458,231 B1 | 10/2002 | Wapner |
| 6,468,313 B1 | 10/2002 | Claeson |
| 6,488,673 B1 | 12/2002 | Laufer et al. |
| 6,493,569 B2 | 12/2002 | Medhkour |
| 6,508,816 B2 | 1/2003 | Shadduck |
| 6,527,761 B1 | 3/2003 | Softesz |
| 6,575,929 B2 | 6/2003 | Sussman |
| 6,579,270 B2 | 6/2003 | Sussman |
| 6,585,639 B1 | 7/2003 | Kotmel |
| 6,588,613 B1 | 7/2003 | Pechenik |
| 6,589,201 B1 | 7/2003 | Sussman |
| 6,592,594 B2 | 7/2003 | Rimbaugh |
| 6,599,311 B1 | 7/2003 | Biggs |
| 6,610,043 B1 | 8/2003 | Ingenito |
| 6,629,951 B2 | 10/2003 | Laufer |
| 6,652,594 B2 | 11/2003 | Francis |
| 6,653,525 B2 | 11/2003 | Ingenito |
| 6,669,694 B2 | 12/2003 | Shadduck |
| 6,676,628 B2 | 1/2004 | Sussman |
| 6,679,264 B1 | 1/2004 | Deem |
| 6,682,520 B2 | 1/2004 | Ingenito |
| 6,692,494 B1 | 2/2004 | Cooper et al. |
| 6,712,812 B2 | 3/2004 | Roschak |
| 6,719,738 B2 | 4/2004 | Mehier |
| 6,755,794 B2 | 6/2004 | Soukup |
| 6,770,070 B1 | 8/2004 | Balbierz |
| 6,776,765 B2 | 8/2004 | Soukup |
| 6,860,847 B2 | 3/2005 | Alferness |
| 6,885,888 B2 | 4/2005 | Rezai |
| 6,901,927 B2 | 6/2005 | Deem |
| 6,904,909 B2 | 6/2005 | Andreas |
| 6,907,881 B2 | 6/2005 | Suki |
| 6,911,028 B2 | 6/2005 | Shadduck |
| 6,986,769 B2 | 1/2006 | Nelson |
| 6,997,189 B2 | 2/2006 | Biggs |
| 7,022,088 B2 | 4/2006 | Keast |
| 7,027,869 B2 | 4/2006 | Danek et al. |
| 7,031,504 B1 | 4/2006 | Argiro |
| 7,083,612 B2 | 8/2006 | Littrup |
| 7,128,748 B2 | 10/2006 | Mooradian |
| 7,136,064 B2 | 11/2006 | Zuiderveld |
| 7,144,402 B2 | 12/2006 | Kuester, III |
| 7,144,588 B2 | 12/2006 | Oray |
| 7,174,644 B2 | 2/2007 | Critelli et al. |
| 7,175,644 B2 | 2/2007 | Cooper et al. |
| 7,192,400 B2 | 3/2007 | Campbell |
| 7,198,635 B2 | 4/2007 | Daneck |

(56) References Cited

U.S. PATENT DOCUMENTS

| | | |
|---|---|---|
| 7,233,820 B2 | 6/2007 | Gilboa |
| 7,235,070 B2 | 6/2007 | Vanney |
| 7,335,195 B2 | 2/2008 | Mehier |
| 7,347,859 B2 | 3/2008 | Garabedian |
| 7,412,977 B2 | 8/2008 | Fields |
| 7,422,563 B2 | 9/2008 | Roschak |
| 7,422,584 B2 | 9/2008 | Loomas |
| 7,425,212 B1 | 9/2008 | Danek et al. |
| 7,462,162 B2 | 12/2008 | Phan |
| 7,628,789 B2 | 12/2009 | Soltesz |
| 7,708,712 B2 | 5/2010 | Phan |
| 7,740,017 B2 | 6/2010 | Daneck |
| 7,756,563 B2 | 7/2010 | Higgins et al. |
| 7,778,704 B2 | 8/2010 | Rezai |
| 7,815,590 B2 | 10/2010 | Cooper |
| 7,819,908 B2 | 10/2010 | Ingenito |
| 7,889,905 B2 | 2/2011 | Higgins et al. |
| 7,906,124 B2 | 3/2011 | Laufer |
| 7,913,698 B2 | 3/2011 | Barry |
| 7,913,898 B2 | 3/2011 | Barry et al. |
| 7,985,187 B2 | 7/2011 | Wibowo |
| 7,993,323 B2 | 8/2011 | Barry et al. |
| 8,002,740 B2 | 8/2011 | Willink |
| 8,088,127 B2 | 1/2012 | Mayse et al. |
| 8,172,827 B2 | 5/2012 | Deem |
| 8,187,269 B2 | 5/2012 | Shadduck |
| 8,251,070 B2 | 8/2012 | Daneck |
| 8,292,882 B2 | 10/2012 | Daneck |
| 8,322,335 B2 | 12/2012 | Barry et al. |
| 8,409,167 B2 | 4/2013 | Roschak |
| 8,444,636 B2 | 5/2013 | Shadduck et al. |
| 8,585,645 B2 | 11/2013 | Barry |
| 8,608,724 B2 | 12/2013 | Roschak |
| 8,628,495 B2 | 1/2014 | Horton et al. |
| 8,709,034 B2 | 4/2014 | Keast et al. |
| 8,734,380 B2 | 5/2014 | Barry |
| 8,784,400 B2 | 7/2014 | Roschak |
| 8,858,549 B2 | 10/2014 | Shadduck |
| 8,900,223 B2 | 12/2014 | Shadduck |
| 9,037,215 B2 | 5/2015 | Higgins et al. |
| 9,050,076 B2 | 6/2015 | Barry et al. |
| 9,133,858 B2 | 9/2015 | Macchia et al. |
| 9,265,468 B2 | 2/2016 | Rai et al. |
| 9,913,969 B2 | 3/2018 | Roschak |
| 10,064,697 B2 | 9/2018 | Sharma et al. |
| 2002/0077516 A1 | 6/2002 | Flanigan |
| 2002/0111386 A1 | 8/2002 | Michael et al. |
| 2002/0112723 A1 | 8/2002 | Schuster et al. |
| 2002/0177846 A1 | 11/2002 | Muller |
| 2003/0099279 A1 | 5/2003 | Venkatasubramanian et al. |
| 2003/0181922 A1 | 9/2003 | Alferness |
| 2003/0233099 A1 | 12/2003 | Danaek et al. |
| 2004/0031494 A1 | 2/2004 | Danek et al. |
| 2004/0038868 A1 | 2/2004 | Ingenito |
| 2004/0047855 A1 | 3/2004 | Ingenito |
| 2004/0055606 A1 | 3/2004 | Hendricksen |
| 2004/0068306 A1 | 4/2004 | Shadduck |
| 2004/0199226 A1 | 10/2004 | Shadduck |
| 2004/0200484 A1 | 10/2004 | Springmeyer |
| 2004/0244803 A1 | 12/2004 | Tanaka |
| 2005/0016530 A1 | 1/2005 | McCutcheon |
| 2005/0066974 A1 | 3/2005 | Fields |
| 2005/0166925 A1 | 8/2005 | Wilson |
| 2005/0171396 A1 | 8/2005 | Pankratov |
| 2005/0171582 A1 | 8/2005 | Matlock |
| 2005/0203483 A1 | 9/2005 | Perkins |
| 2005/0215991 A1 | 9/2005 | Altman |
| 2005/0222485 A1 | 10/2005 | Shaw |
| 2006/0004400 A1 | 1/2006 | McGurk |
| 2006/0047291 A1 | 3/2006 | Barry |
| 2006/0100619 A1 | 5/2006 | McClurken |
| 2006/0130630 A1 | 6/2006 | Barry |
| 2006/0135955 A1 | 6/2006 | Shadduck |
| 2006/0162731 A1 | 7/2006 | Wondka |
| 2006/0200076 A1 | 9/2006 | Gonzalez |
| 2006/0224154 A1 | 10/2006 | Shadduck |
| 2007/0032785 A1 | 2/2007 | Diederich |
| 2007/0036417 A1 | 2/2007 | Argiro |
| 2007/0068530 A1 | 3/2007 | Pacey |
| 2007/0091087 A1 | 4/2007 | Zuiderveld |
| 2007/0092864 A1 | 4/2007 | Reinhardt |
| 2007/0102011 A1 | 5/2007 | Danek |
| 2007/0106292 A1 | 5/2007 | Kaplan |
| 2007/0109299 A1 | 5/2007 | Peterson |
| 2007/0112349 A1 | 5/2007 | Danek |
| 2007/0118184 A1 | 5/2007 | Danek |
| 2007/0137646 A1 | 6/2007 | Weinstein |
| 2007/0293853 A1 | 12/2007 | Truckai |
| 2008/0033493 A1 | 2/2008 | Deckman |
| 2008/0132826 A1 | 6/2008 | Shadduck |
| 2008/0249439 A1 | 10/2008 | Tracey et al. |
| 2009/0043301 A1 | 2/2009 | Jarrard |
| 2009/0118538 A1 | 5/2009 | Pizzocaro et al. |
| 2009/0138001 A1 | 5/2009 | Barry et al. |
| 2009/0149646 A1 | 6/2009 | Hoey |
| 2009/0149846 A1 | 6/2009 | Hoey et al. |
| 2009/0149897 A1 | 6/2009 | Dacey, Jr. et al. |
| 2009/0156895 A1 | 6/2009 | Higgins et al. |
| 2009/0192508 A1 | 7/2009 | Laufer et al. |
| 2009/0216220 A1 | 8/2009 | Hoey |
| 2009/0306640 A1 | 12/2009 | Glaze et al. |
| 2009/0306644 A1* | 12/2009 | Mayse .................. A61B 18/18 606/33 |
| 2009/0312753 A1 | 12/2009 | Shadduck |
| 2010/0094270 A1 | 4/2010 | Sharma |
| 2010/0204688 A1 | 8/2010 | Hoey |
| 2010/0256714 A1 | 10/2010 | Springmeyer |
| 2010/0262133 A1 | 10/2010 | Hoey |
| 2010/0310146 A1 | 12/2010 | Higgins et al. |
| 2011/0077628 A1 | 3/2011 | Hoey |
| 2011/0118725 A1* | 5/2011 | Mayse ..................... A61N 7/00 606/33 |
| 2011/0160648 A1 | 6/2011 | Hoey |
| 2011/0257644 A1* | 10/2011 | Barry .................... A61B 18/04 606/28 |
| 2011/0270031 A1 | 11/2011 | Frazier |
| 2011/0301587 A1 | 12/2011 | Deem |
| 2011/0319958 A1 | 12/2011 | Simon et al. |
| 2012/0016363 A1 | 1/2012 | Mayse |
| 2012/0016364 A1 | 1/2012 | Mayse |
| 2012/0289776 A1* | 11/2012 | Keast ................... A61B 17/221 600/106 |
| 2013/0006231 A1 | 1/2013 | Sharma |
| 2013/0267939 A1 | 10/2013 | Barry et al. |
| 2013/0324987 A1 | 12/2013 | Leung et al. |
| 2014/0025057 A1 | 1/2014 | Hoey et al. |
| 2014/0275952 A1 | 9/2014 | Monroe et al. |
| 2014/0276713 A1 | 9/2014 | Hoey et al. |
| 2015/0094607 A1 | 4/2015 | Barry et al. |
| 2015/0230852 A1 | 8/2015 | Barry |
| 2016/0180629 A1 | 6/2016 | Rai et al. |
| 2016/0220297 A1 | 8/2016 | Kroon et al. |
| 2016/0287307 A1* | 10/2016 | Clark .................... A61B 5/6852 |
| 2016/0310200 A1 | 10/2016 | Wang |
| 2016/0374710 A1 | 12/2016 | Sinelnikov et al. |
| 2018/0036084 A1 | 2/2018 | Krimsky |
| 2018/0318002 A1 | 11/2018 | Barry et al. |
| 2019/0069948 A1 | 3/2019 | Herth et al. |
| 2019/0343579 A1 | 11/2019 | Tandri et al. |

FOREIGN PATENT DOCUMENTS

| | | |
|---|---|---|
| EP | 1143864 | 2/2004 |
| EP | 1173103 | 10/2005 |
| EP | 1326549 | 12/2005 |
| EP | 1326548 | 1/2006 |
| EP | 1485033 | 8/2009 |
| WO | 2000/11927 | 3/2000 |
| WO | 2001/02042 | 1/2001 |
| WO | 2002/069821 | 9/2002 |
| WO | 2003/070302 | 8/2003 |
| WO | 2003/086498 | 10/2003 |
| WO | 2005/025635 | 3/2005 |

(56) References Cited

FOREIGN PATENT DOCUMENTS

| | | |
|---|---|---|
| WO | 2005/102175 | 11/2005 |
| WO | 2006/003665 | 1/2006 |
| WO | 2006/052940 | 5/2006 |
| WO | 2006/053308 | 5/2006 |
| WO | 2006/053309 | 5/2006 |
| WO | 2006/080015 | 8/2006 |
| WO | 2006/116198 | 11/2006 |
| WO | 2008/051706 | 5/2008 |
| WO | 2009/009236 | 1/2009 |
| WO | 2009/009398 | 1/2009 |
| WO | 2009/015278 | 1/2009 |
| WO | 2009/137819 | 11/2009 |
| WO | 2010/042461 | 4/2010 |
| WO | 2011/056684 | 5/2011 |
| WO | 2011/060201 | 5/2011 |
| WO | 2011060200 | 5/2011 |
| WO | 2011/127216 | 10/2011 |

OTHER PUBLICATIONS

Carpenter III et al.; Comparison of endoscopic cryosurgery and electrocoagulation of bronchi; Trans. Amer. Acad. Opth., vol. 84; No. 1; pp. ORL-313-ORL-323; Jan. 1977.

clinical trials.gov.; Study of the AeriSeal System for HyPerinflation Reduction in Emphysema; 4 pages; Nov. 5, 2014; retrieved from the internet (http://clinicaltrials.gov/show/N.

Coda, et al., "Effects of pulmonary reventilation on gas exchange after cryolytic disobstruction of endobronchial tumors," Minerva Medical, vol. 72, pp. 1627-1631, Jun. 1981.

Delaunois; Anatomy and physiology of collateral respiratory pathways; Eur. Respir. J.; 2(9); pp. 893-904; Oct. 1989.

Eyal et al.; The acute effect of pulmonary burns on lung mechanics and gas exchange in the rabbit; Br. J. Anaesth.; vol. 47; pp. 546-552; (year of publication is sufficiently, Date: 1975.

Ferlay et al.; GLOBOCAN 2008 v1.2, Cancer Incidence and Mortality Worldwide: IARC CancerBase No. 10.

Fishman et al., A randomized trial comparing lung-volume-reduction surgery with medical therapy for severe emphysema, N Engl J Med, vol. 348, No. 21, pp. 2059-2073, May 22, 2003.

Goldberg et al.; Radiofrequency tissue ablation in the rabbit lung: Efficacy and complications; Acad. Radiol.; vol. 2; pp. 776-784; Sep. 1995.

Herth et al., Efficacy predictors of lung volume reduction with zephyr valves in a european cohort, Eur.Respir. J.: 39(6); pp. 1334-1342, Jun. 2012.

Homasson, et al., "Bronchoscopic cryotherapy for airway strictures caused by tumors," Chest, vol. 90, No. 2, Aug. 1986.

Kinsella, et al., "Quantitation of emphysema by computer tomography useing a densitymask program and correlation with pulmonary function tests," Chest 97(2), Feb. 1990.

Looga, R., "Mechanism of changes in the respiratory and cardiovascular reflexes from the lungs associated with intrapulmonary steam burns," Eng.Trans from Byulleten Experimental noi Biologii I Meditsiny: vol. 6, No. 6, Jun. 1966.

Marasso, et al., "Cryosurgery in bronchoscopic treatment of tracheobrachial stenosis," Chest, vol. 103, No. 2, Feb. 1993.

Marasso, et al., "Radiofrequency resection of bronchial tumors in combination with cryotherapy; evaluation of a new technique," Thorax, vol. 53, 1998.

Mathur, et al., "Fiberoptic bronchoscopic cryotherapy in the management of trachebronchial obstruction," Chest, vol. 110, No. 3, Sep. 1996.

Morice, et al., "Endobrinchial argon plasma coagulation for treatment of hemotysis and neoplastic airway obstruction," Chest, vol. 119, No. 3, Mar. 2001.

Moritz, et al., "The effects of inhaled heat on the air passage and lungs," American J. of Pathology, vol. XXI, 1944.

Moulding, et al., "Preliminary studies for achieving transcervical oviduct occlusion by hot water or low pressure steam," Advances in Planned Parenthood, vol. 12 No. 2, 1977.

National Lung Screening Trial Research Team, "Reduced Lung Cancer mortality with low dose computed tomographic screening," N. Eng. J.Med, 365(5), Aug. 2011.

Pracht, Adam, "VIDA takes new approach," Iowa City Press Citizen, Sep. 12, 2005.

Quin, J., "Use of neodymium yttrium aluminum garnet laser in long term palliation of airway obstruction," Connecticut Medicine, vol. 59, No. 7, Jul. 1995.

Sciurba et al., "A randomized study of endobronchial valves for advanced emphysema," N.Eng J. Med, 363(13), Sep. 2010.

Shah, et al., "Collateral ventilation and selection of techniques for bronchscopic lung volume reduction," Thorax, 67 (4), Apr. 2012.

Slebos, et al., "Bronchoscopic lung volume reduction coil treatment of patients with sever heterogeneous emphysema," Chest, 142(3), Sep. 2012.

Sutedja, et al, "Bronchoscopic treatment of lung tumors," Elsevier, Lung Cancer, Jul. 11, 1994.

Van De Velde, "Vapo-cauterization of the uterus," Amer.J.Med, Sci vol. CXVII, 1899.

Vorre, et al., "Morphology of tracheal scar after resection with C02 laser and high-frequency cutting loop," Acta Otolarynaol (Stockh), vol. 107, 1989.

Tschirren, "Interthoracic Airway Trees: Segmentation and Airway Morphology Analysis from Low Dose CT Scans," IEEE Transactions on Medical Imaging, vol. 24, No. 12, 2005.

Kang, Li, "Efficient optimal net surface detection for image segmentation—from theory to practice," M.Sc.Thesis, The University of Iowa, Dec. 2003.

Tschirren, J., "Segmentation, anatomical labeling, branchpoint matching, and quantitative analysis of human airway trees in volumetric CT images," Ph.D, Thesis, The University of Iowa, Aug. 2003, Part 1.

Tschirren, J., "Segmentation, anatomical labeling, branchpoint matching, and quantitative analysis of human airway trees in volumetric CT images," Ph.D. Thesis, The University of Iowa, Aug. 2003, Part 2.

Tschirren, J., "Segmentation, anatomical labeling, branchpoint matching, and quantitative analysis of human airway trees in volumetric CT images," Ph.D. Thesis, The University of Iowa, Aug. 2003, Part 3.

Tschirren, J., "Segmentation, anatomical labeling, branchpoint matching, and quantitative analysis of human airway trees in volumetric CT images," Slides from Ph.D. Defense, The University of Iowa, Jul. 10, 2003, Part 1.

Tschirren, J., "Segmentation, anatomical labeling, branchpoint matching, and quantitative analysis of human airway trees in volumetric CT images," Slides from Ph.D. Defense, The University of Iowa, Jul. 10, 2003, Part 2.

Blacker, G. F.; Vaporization of the uterus; J. of Obstetrics and Gynaecology; vol. 33; pp. 488-511; 1902.

clinical trials.gov.; Study of the AeriSeal System for HyPerinflation Reduction in Emphysema; 4 pages; Nov. 5, 2014; retrieved from the internet (http://clinicaltrials.gov/show/NCT01449292).

Cox et al., "Bronchial Thermoplasty for Asthma." American Journal of Respiratory Critical Care Medicine 173: 965-969 (2006).

\* cited by examiner

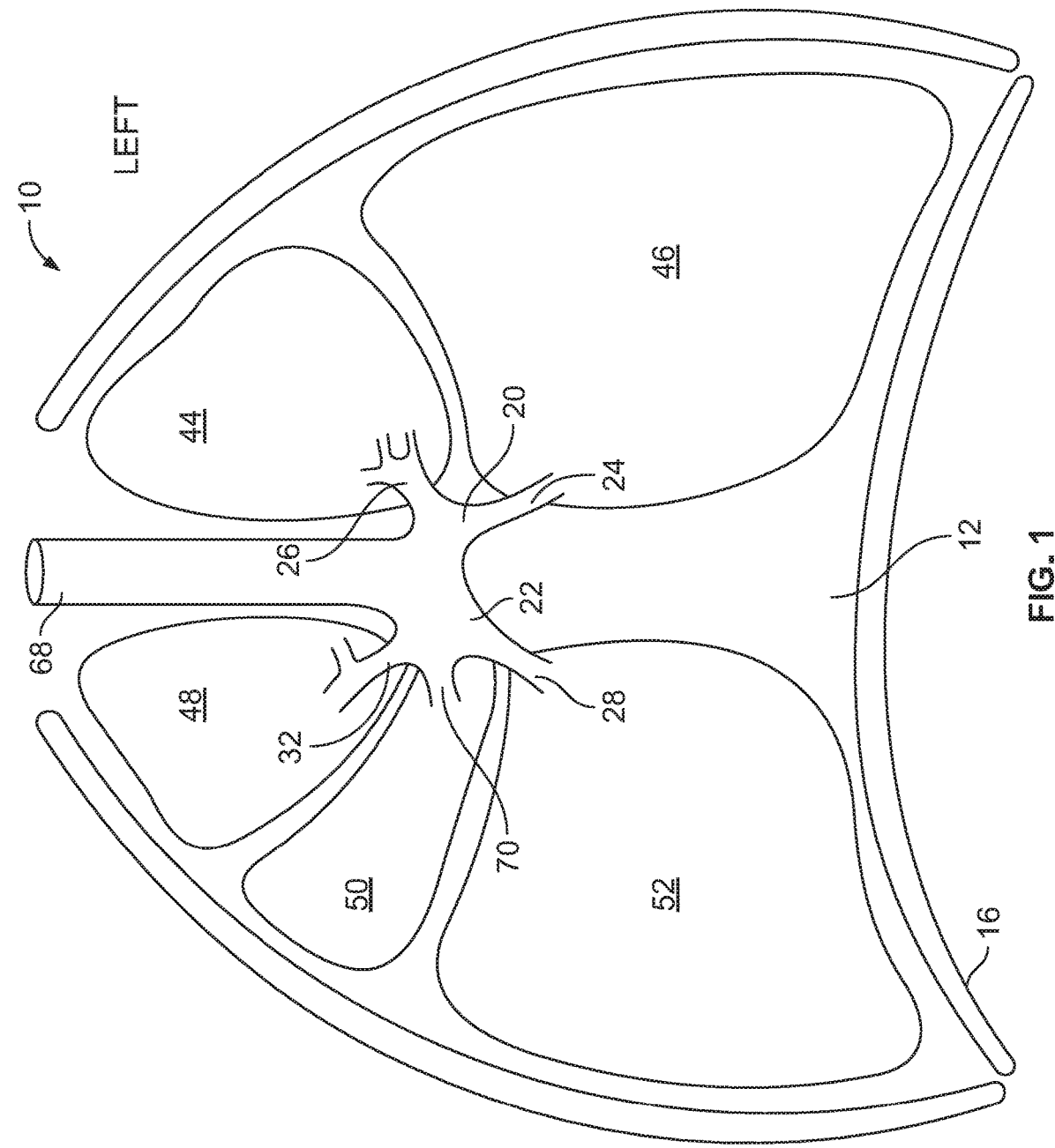

EXTRA-AIRWAY VAPOR ABLATION FOR TREATING AIRWAY CONSTRICTION IN PATIENTS WITH ASTHMA AND COPD

CROSS-REFERENCE TO RELATED APPLICATIONS

This application claims priority to provisional application No. 62/502,050, filed May 5, 2017, and entitled "EXTRA-AIRWAY VAPOR ABLATION FOR TREATING AIRWAY CONSTRICTION IN PATIENTS WITH ASTHMA AND COPD."

BACKGROUND OF THE INVENTION

Asthma and chronic obstructive pulmonary disease (COPD) are respiratory conditions affecting numerous people. People suffering from asthma and COPD experience airway constriction (bronchoconstriction) in the lungs, making breathing difficult, uncomfortable, and potentially life threatening.

Various approaches to treat patients with airway constriction include systemic and interventional-based techniques. Examples of systemic-based techniques include use of steroids and other anti-inflammatory drugs which work to reduce swelling and mucus production in the airways. However, prolonged use of inhaled corticosteroids has potential to cause side effects. Examples of potential side effects include impaired growth in children, decreased bone mineral density, skin thinning and bruising, and cataracts. Dahl R. "Systemic side effects of inhaled corticosteroids in patients with asthma," Respir Med. 2006 August; 100(8):1307-17. Epub 2006 Jan. 18.

Examples of interventional-based techniques include bronchial thermoplasty in which radiofrequency (RF) energy is applied to the interior surface of the airway wall, heating the airway and reducing the amount of smooth muscle present in the airway wall. Cox G., M. D., McWilliams A., FitzGerald J. M., and Lam S. (2006). "Bronchial Thermoplasty for Asthma." American Journal of Respiratory Critical Care Medicine 173: 965-969. Another example is targeted lung denervation in which RF energy is projected through the airway wall to ablate and permanently interrupt the function of the airway nerves. See Holaira™ Lung Denervation System (manufactured by Holaira Inc., Minneapolis, Minn.).

A shortcoming with the above described interventional-based techniques, however, is the temperature closer to the heat element shall increase more rapidly than the temperature farther from the heat element. The non-uniform temperature distribution increases the risk of collateral damage to non-target or healthy tissues near the heat source when trying to heat more remote target tissue.

Another shortcoming is that each technology is limited to ablating only one type of tissue: either the muscle (thermoplasty) or the nerve (targeted lung denervation).

Accordingly, there is still a need for minimally invasive approaches to effectively ablate extra-airway target lung regions while minimizing collateral damage to other structures.

There is also a need to more quickly and more effectively ablate the extra-airway structures.

SUMMARY OF THE INVENTION

A method for ablating a target tissue outside of an airway in a patient's lung comprises advancing a distal section of a catheter into contact with the target tissue outside of the airway. The position of the distal section of the catheter is assessed to determine whether the catheter is in contact with the target tissue. Vapor is delivered into the target tissue through an egress port with a sufficient amount of energy to ablate the target tissue.

In embodiments, vapor is directed at the nerves and or smooth muscles surrounding the constricted airways.

In embodiments, the distal section of the vapor delivery catheter has a face surface in which at least one egress port is located. The face surface is manipulated into a position such that the egress port is aimed towards the exterior surface of the target tissue (e.g., the nerves or smooth muscles surrounding the airway). The face surface can be further manipulated into a position such that the egress port is aimed towards and contacting the exterior surface of the target tissue.

In embodiments, the distal section of the catheter is adapted to penetrate the airway wall and be advanced to the target tissue. In other embodiments, the distal section of the catheter is advanced through a pre-existing hole, passageway, or tubular appliance towards the target tissue. Then, the target is ablated.

In embodiments, a method for treating cancer in a lung of a patient includes identifying a tumor in the lung; and identifying a blood vessel that feeds the tumor. The method further includes advancing a distal section of the vapor delivery catheter into the lung along an airway, and further advancing the distal section of the vapor delivery catheter from the airway into contact with the blood vessel outside of the airway. The position of the catheter is assessed to determine whether the catheter is in position to ablate the blood vessel. After the position of the catheter is confirmed, the method includes delivering vapor to the blood vessel through the egress port with a sufficient amount of energy to ablate the blood vessel.

In another embodiment, a method for ablating a target tissue outside of an airway in a patient's lung comprises advancing a distal section of a catheter into contact with the target tissue outside of the airway. The position of the distal section of the catheter is assessed to determine whether the catheter is in contact with the target tissue. Energy is delivered to the target tissue from the distal section sufficient to ablate the target tissue. The target tissue may be ablated or otherwise destroyed by causing target tissue's temperature to hit a lethal range beyond which the tissue is not functional or viable. In preferred embodiments, delivery of the energy is performed using a condensable vapor.

The description, objects and advantages of the present invention will become apparent from the detailed description to follow, together with the accompanying drawings.

BRIEF DESCRIPTION OF THE DRAWINGS

FIG. 1 illustrates a human respiratory system;

DETAILED DESCRIPTION OF THE INVENTION

Figure 2A:
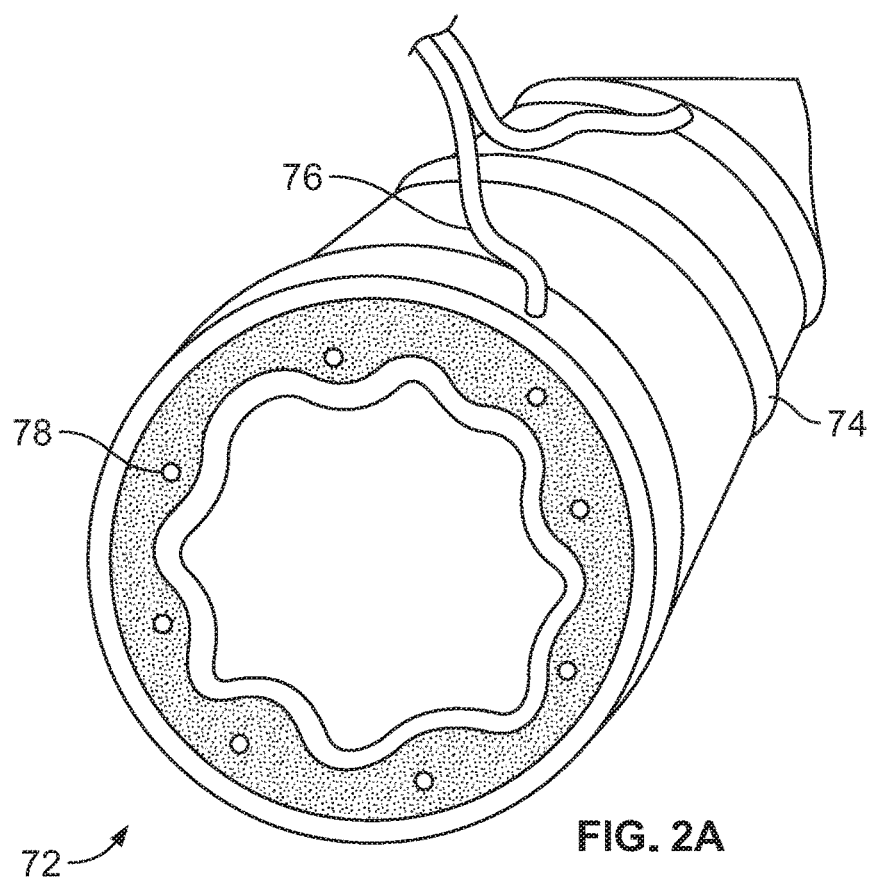
FIGS. 2A, 2B illustrate an airway in the respiratory system in a normal and asthmatic state respectively.

Before the present invention is described in detail, it is to be understood that this invention is not limited to particular variations set forth herein as various changes or modifications may be made to the invention described and equivalents may be substituted without departing from the spirit and scope of the invention. As will be apparent to those of skill in the art upon reading this disclosure, each of the individual embodiments described and illustrated herein has discrete components and features which may be readily separated from or combined with the features of any of the other several embodiments without departing from the scope or spirit of the present invention. In addition, many modifications may be made to adapt a particular situation, material, composition of matter, process, process act(s) or step(s) to the objective(s), spirit or scope of the present invention. All such modifications are intended to be within the scope of the claims made herein.

Methods recited herein may be carried out in any order of the recited events which is logically possible, as well as the recited order of events. Furthermore, where a range of values is provided, it is understood that every intervening value, between the upper and lower limit of that range and any other stated or intervening value in that stated range is encompassed within the invention. Also, it is contemplated that any optional feature of the inventive variations described may be set forth and claimed independently, or in combination with any one or more of the features described herein.

All existing subject matter mentioned herein (e.g., publications, patents, patent applications and hardware) is incorporated by reference herein in its entirety except insofar as the subject matter may conflict with that of the present invention (in which case what is present herein shall prevail). The referenced items are provided solely for their disclosure prior to the filing date of the present application.

Reference to a singular item, includes the possibility that there are plural of the same items present. More specifically, as used herein and in the appended claims, the singular forms "a," "an," "said" and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Last, it is to be appreciated that unless defined otherwise, all technical and scientific terms used herein have the same meaning as commonly understood by one of ordinary skill in the art to which this invention belongs.

FIG. 1 illustrates a human respiratory system 10. The respiratory system 10 resides within the thorax 12 that occupies a space defined by the chest wall 14 and the diaphragm 16. The human respiratory system 10 includes left lung lobes 44 and 46 and right lung lobes 48, 50, and 52.

The respiratory system 10 may be characterized by a tree-like structure formed of branched airways including the trachea 68; left and right main stem bronchus 20 and 22 (primary, or first generation) and lobar bronchial branches 24, 26, 28, 30, and 32 (second generation). Segmental and subsegmental branches further bifurcate off the lobar bronchial branches (third and fourth generation). Each bronchial branch and sub-branch communicates with a different portion of a lung lobe, either the entire lung lobe or a portion thereof.

Figure 2B:
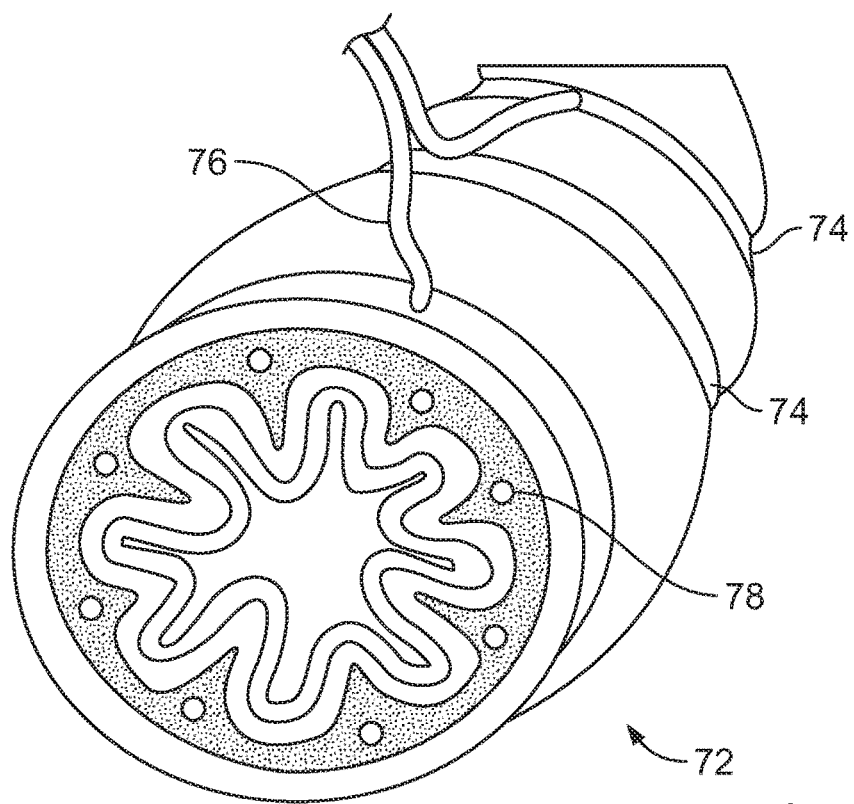

FIGS. 2A, 2B illustrate cross sectional views of an airway in a normal state 72 and asthmatic state 72', respectively. Smooth muscles 74 are shown axially spaced along the airway and are contracted in the asthmatic airway 72'. Nerves 76 communicate with the smooth muscles, and control movement of the smooth muscles 74. Thus, the nerves can affect the size or diameter of the airway passageway by causing the smooth muscles to constrict or expand. Blood vessels 78 are also shown in FIGS. 2A, 2B serving to transport blood therethrough.

Bronchoscopy Approach

Figure 3:
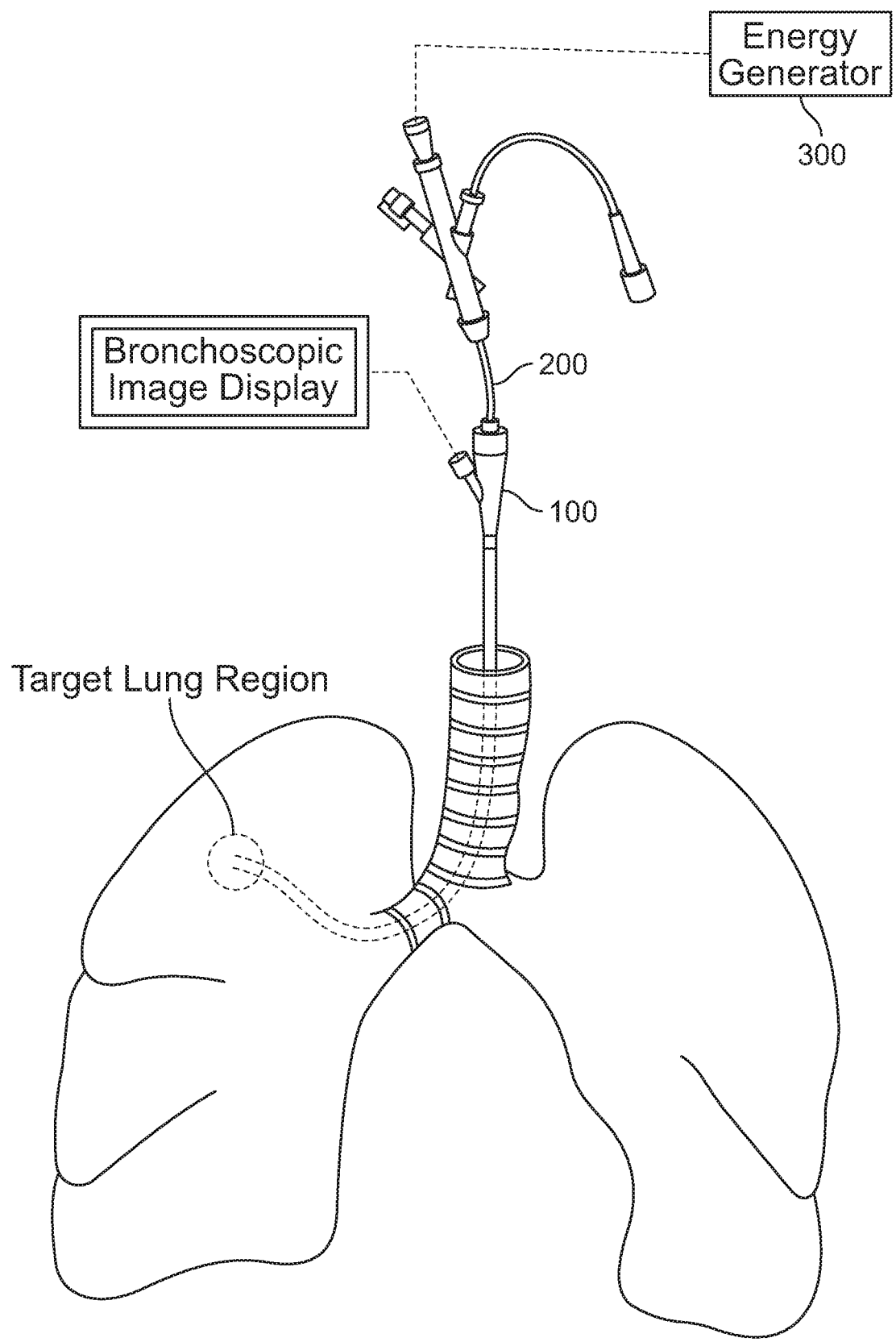
FIG. 3 illustrates a bronchoscopic method for treating lung tissue.

FIG. 3 illustrates a bronchoscopic procedure in accordance with some embodiments of the present invention. FIG. 3 shows a bronchoscope 100 having a working channel into which an energy delivery catheter 200 is inserted. Bronchoscope 100 is inserted into a patient's lungs while the proximal portion of the energy delivery catheter 200 remains outside of the patient. Energy delivery catheter 200 is adapted to operatively couple to an energy generator 300 as further discussed below. Examples of energy delivery catheters include without limitation a condensable vapor ablation catheter as described herein.

Energy Generator

Figure 4:
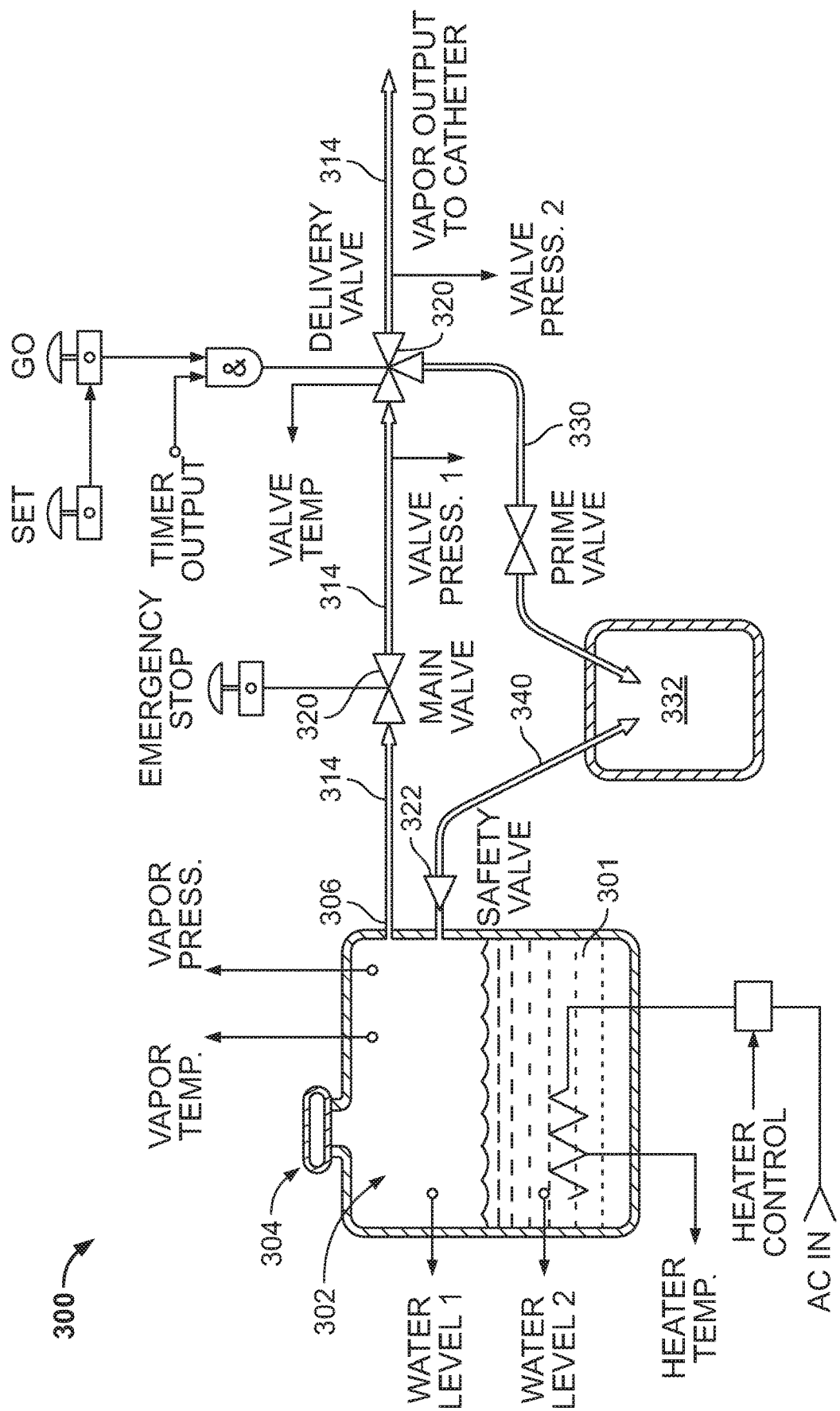
FIG. 4 is a schematic illustration of a vapor generator.

FIG. 4 is a schematic diagram of an energy generator 300 configured as a vapor generator. In embodiments, vapor generator is configured to deliver a controlled dose of vapor to one or more target lung tissues. Vapor generator 300 is adapted to convert a biocompatible liquid 301 (e.g. saline, sterile water or other biocompatible liquid), into a wet or dry vapor, which is then delivered to one or more target tissues. A wet vapor refers to a vapor that contains vaporous forms of the liquid as well as a non-negligible proportion of minute liquid droplets carried over with and held in suspension in the vapor. A dry vapor refers to a vapor that contains little or no liquid droplets. In general, vapor generator 300 is configured to have a liquid capacity between about 1000 to 2500 cc and configured to generate a vapor having a pressure between about 5-100 psig and temperatures between about 100-175° C.

In embodiments, vapor generator 300 is configured as a self-contained, medical-grade generator unit comprising at least a vaporizing unit 302, a vapor inlet 304, and a vapor outlet 306. The vaporizing unit 302 comprises a fluid chamber for containing a fluid 301, preferably a biocompatible, sterile fluid, in a liquid state. In embodiments, vapor outlet 306 is coupled to one or more pipes or tubes 314, which in turn are placed in fluid communication with an energy delivery catheter 200. Vapor flow from vapor generator 300 to a catheter (and specifically a vapor lumen of said catheter) is depicted as a vapor flow circuit 314 wherein flow of the vapor in circuit 314 is indicated by arrows 314 in FIG. 4. In a preferred embodiment, vapor generator is configured to deliver a repeatable dose of vapor to energy delivery catheter 200. Suitable doses of vapor range from 100 to 1000 calories.

Vaporizer unit 302 is configured to heat and vaporize a liquid contained therein. Other components can be incorporated into the biocompatible liquid 301 or mixed into the vapor. For example, these components can be used in order to control perioperative and/or post procedural pain, enhance tissue fibrosis, and/or control infection. Other constituents, for the purpose of regulating vapor temperatures and thus control extent and speed of tissue heating, can be incorporated; for example, in one implementation, carbon dioxide, helium, other noble gases can be mixed with the vapor to decrease vapor temperatures.

Vaporizing unit 302 is also shown having a fluid inlet 304 to allow liquid 301 to be added to the fluid chamber as needed. Fluid chamber can be configured to accommodate or vaporize sufficient liquid as needed to apply vapor to one or more target tissues. Liquid in vaporizing unit 302 is heated and vaporized and the vapor flows into vapor outlet 306. A number of hollow tubular shafts or pipes 314 are adapted to fluidly connect vapor outlet 306 to the catheter 200.

In embodiments, a flexible hollow tube or umbilical-like cord extends from the generator 300 and terminates in a handle (not shown). The handle is adapted to operatively couple to a variety of types of energy delivery catheters via a hub assembly (such as hub assembly 214 shown in FIG. 5 and discussed herein). In embodiments, the hub assembly or other connecting means is configured to allow for a secure, fluidly sealed, and quick release between the catheter and generator handle. Examples of suitable quick connect and release mechanisms include, without limitation, Luer Lock hub assemblies and fittings.

In embodiments, a catheter and vapor generator are configured to be directly coupled to one another via mating connectors. Vapor delivery is controlled by the generator, a controller external to the generator, or actuating buttons and mechanisms on the catheter itself. For example, the catheter may comprise a handpiece portion to control vapor doses.

Preferably, there is little or no vapor-to-liquid transition during movement of the vapor through vapor flow circuit 314. Vapor flow through vapor flow circuit 314 is unidirectional (in the direction of arrows 314), accordingly one or more isolation valves 320 are incorporated in vapor flow circuit 314. Isolation valves 320, which are normally open during use of generator 300, serve to minimize vapor flow in a direction opposite that of the vapor flow circuit 314.

A priming line 330, branching from main vapor flow circuit 314, is provided to minimize or prevent undesirable liquid-state water formation during vapor flow through vapor flow circuit 314. Pressure and temperature changes along vapor flow circuit 314 can affect whether the vapor is sustainable in a vapor state or condensed back into a liquid. Priming line 330 is provided to equalize temperatures and/or pressures along vapor flow circuit 314 in order to minimize or prevent undesirable liquid-state transition of the vapor during its progression through vapor flow circuit 314. In one embodiment, an initial "purge" or "priming" procedure can be performed prior to delivery of a therapeutic vapor dose in order to preheat flow circuit 314 thus maintaining a constant temperature and pressure in the main vapor flow circuit 314 prior to delivery of a vapor to the target lung tissue.

As shown in FIG. 4, priming line 330 terminates at evaporator 332, which is adapted to either house undesirable liquid in a collection unit (not shown) located within generator 300. In one embodiment, collection unit is adapted to house the liquid until a user or clinician is able to empty said collection unit. Alternatively, evaporator 332 is configured to evaporate and expel said undesirable liquid into the ambient air. Baffle plates (not shown) or other like means can be incorporated in evaporator 332 to facilitate maximal vapor-to-liquid transition. It should be understood that other suitable evaporator configurations could be included to facilitate vapor-to-liquid transition during a priming procedure of lines 314.

A number of sensors, operatively connected to a controller, can be incorporated into vapor generator 300, for example, in the liquid chamber, or along any point in vapor flow circuit 314. Water level sensors, adapted to monitor the water level in the liquid chamber, can be included. These water level sensors are configured as upper and lower security sensors to sense or indicate when a liquid level in the fluid chamber is below or above a set fluid level. For example, if a water level in the fluid chamber falls below the level of a lower water control sensor, the controller can be configured to interrupt the operation of the vapor generator 300.

In yet another embodiment, pressure sensors, or manometers, can be included in vaporizing unit 302, or at various points along the vapor flow circuit 314, to measure the liquid or vapor pressures at various discrete locations and/or to measure vapor pressures within a defined segment along circuit 314. One or more control valves 320 can also be installed at various points in the vapor flow circuit 314 to control vapor flow, for instance, to control or increase the vapor flow or vapor flow rates in vapor flow circuit 314.

In yet another embodiment, a safety valve 322 can be incorporated into the liquid chamber of vaporizing unit 302 and coupled to a vapor overflow line 340 if the need for removing or venting vaporizing unit 302 arises during generator 300 operation.

Although the vapor generator is described above having various specific features, the components and configurations of the vapor generator and catheter systems may vary. Additional vapor ablation systems are described in, for example, U.S. Patent Publication No. 2015/0094607 to Barry et al., and U.S. Pat. No. 7,913,698 to Barry et al., and U.S. Pat. No. 8,322,335 to Barry et al., and U.S. Pat. No. 7,993,323 to Barry et al.

In other embodiments, a condensable vapor is created in the handle portion of the catheter system. Consequently, a separate vapor generator unit is not required. Systems including a resistive heater are described in, for example, U.S. Patent Publication No. 2016/0220297 to Kroon et al. and U.S. Patent Publication No. 2014/0276713 to Hoey et al. Indeed, embodiments of the invention include a wide range of mechanisms to create and transport vapor through the working catheter as described herein.

Vapor Ablation Catheter

Figure 5:
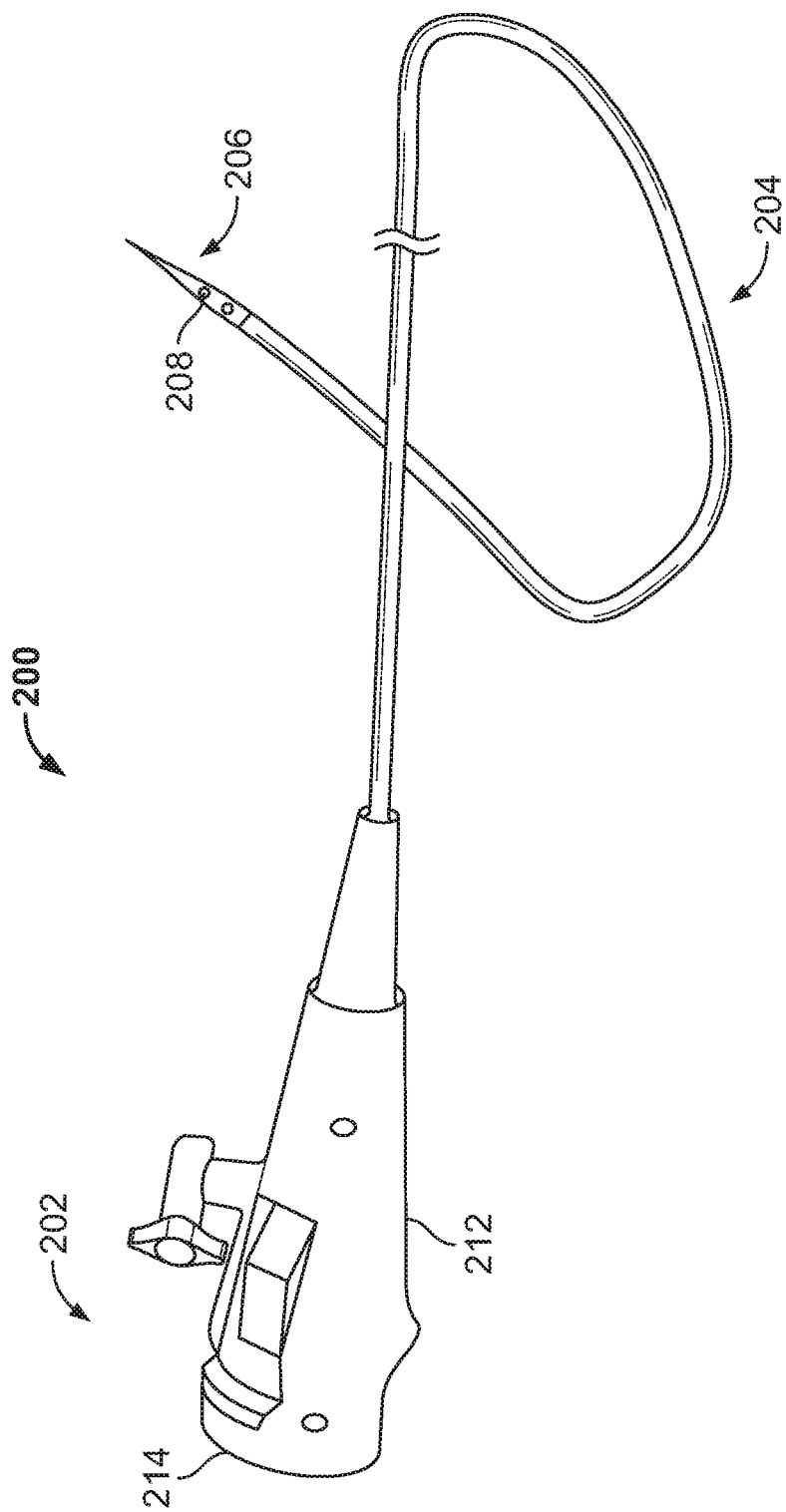
FIG. 5 is an illustration of a vapor ablation catheter.

FIG. 5 illustrates a vapor ablation catheter 200 in accordance with one embodiment of the invention. Catheter 200 is shown having a proximal section 202, intermediate section 204, and distal end section 206. Proximal section 202 can include a handpiece portion 212 and hub 214 which may be connected to the generator as described above. Intermediate section 204 is flexible and continues to distal end section 206. Examples of suitable materials for the catheter shaft include polyimide, PEBAX, silicone, PEEK, and stainless steel braiding.

The distal end section 206 is shown having a pointed tip and a plurality of egress ports 208 for vapor to be directed towards the target tissue. In embodiments, the tip is rigid, sharp, and adapted to penetrate tissue. Examples of suitable materials for the tip of the catheter include stainless steel, Nitinol, and PEEK. At least one egress port 208 is desirable, however, the number of egress ports may range from 1-20, and more preferably 6-12.

The shape of the egress port is shown as a circle. However, the shape and size of the egress ports may vary. In embodiments, the egress port has a circular shape and a diameter in the range of 0.1 to 2 mm.

FIG. 5 shows the egress ports 208 on one lateral surface, face, side, or facet of the tip. The vapor may thus be aimed in solely one direction. However, in other embodiments, the egress ports are spaced about the circumference of the distal end section such that the vapor may be directed radially in all directions from the shaft. In yet other embodiments, the egress port(s) are located on the end of the catheter tip and send the vapor in an axial direction.

Additional examples of vapor delivery catheter configurations are described in the literature. Another example of a vapor catheter having components and structures which may be combined with the subject invention is described in U.S. Pat. No. 8,444,636 to Shadduck and Hoey; and U.S. Patent Publication No. 2014/0025057 to Hoey and Shadduck. The catheter and tip configuration may vary widely and the invention is only intended to be limited as recited in the appended claims.

Asthma Treatment

Figure 6A:
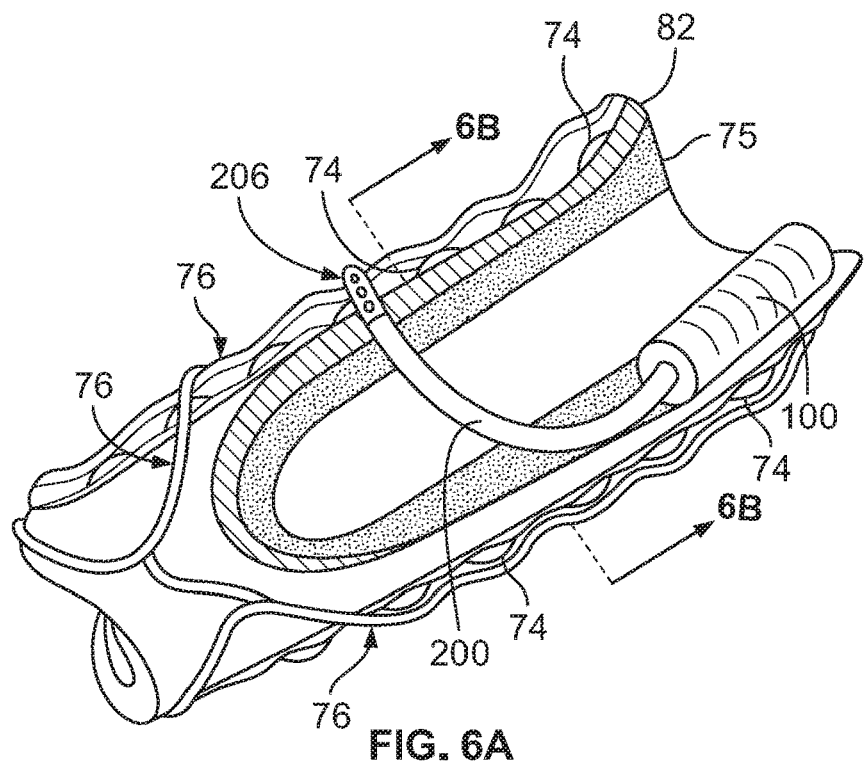
FIG. 6A is an illustration of a vapor ablation catheter advanced to a target tissue for treating asthma.

FIG. 6A illustrates use of a vapor ablation catheter 200 to treat an asthmatic airway 82. The airway is shown in a constricted state due to the contraction of smooth muscles 74, and the condition is further exacerbated by the presence of an increased mucus layer 75.

FIG. 6A also shows catheter 200 having been advanced from the bronchoscope 100. Distal end section 206 is shown passing through the airway wall 82, between smooth muscle segments 74, and facing towards or in contact with nerve portion 76.

Figure 6B:
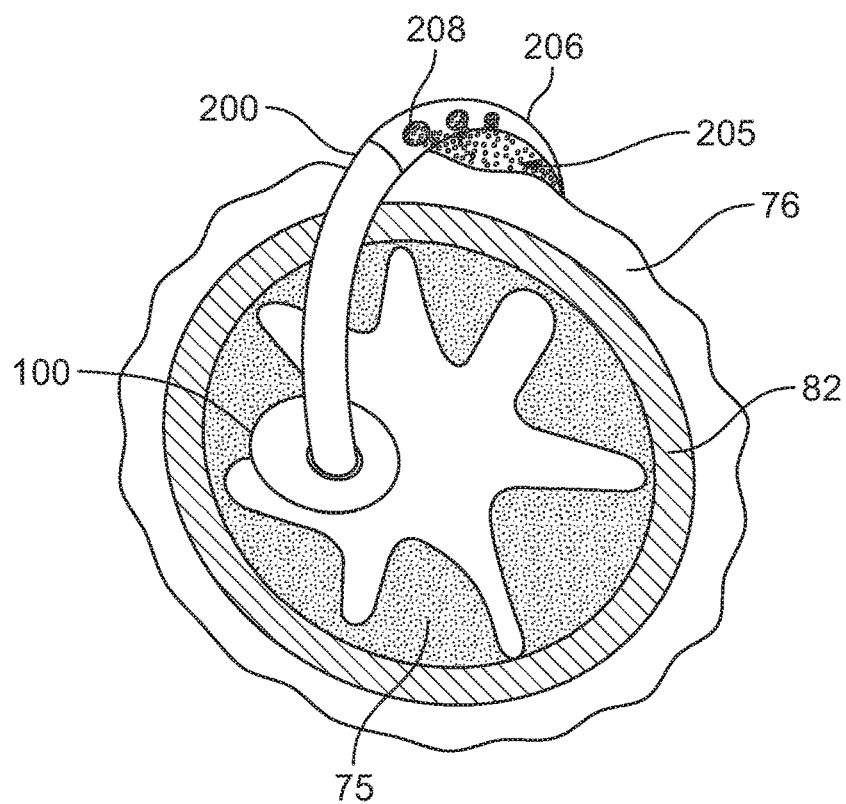
FIG. 6B is a cross sectional view of the airway anatomy and vapor ablation catheter shown in FIG. 6A taken along line 6B-6B.

FIG. 6B is a cross section illustration of FIG. 6A, taken along line 6B-6B. Distal end section 206 of the catheter is shown advanced outside of the airway, and adjusted to face nerve portion 76. Egress ports 208 are shown aimed or directed towards the exterior surface of the nerve 76, and in some embodiments, the smooth muscle.

Vapor 205 is shown delivered from the egress ports 208 towards the nerve 76, and the smooth muscle 74 surrounding the outside of the airway. As mentioned herein, and without intending to be bound to theory, heating the nerve and smooth muscles surrounding the airway prevents the narrowing of the airway characteristic of an asthma attack.

It should also be appreciated that the embodiment shown in FIG. 6B demonstrates the distal end 206 being located in close proximity (e.g., within 5 mm) and perhaps even making contact with the exterior surface of the nerve 76. The vapor 205 is directed towards the target and, due to its gaseous state, tends to follow the target airway boundary, creating a safer, faster, and more precise energy delivery than previous methods (e.g., a heat source placed against the interior surface of the airway wall 82).

Figure 6C:
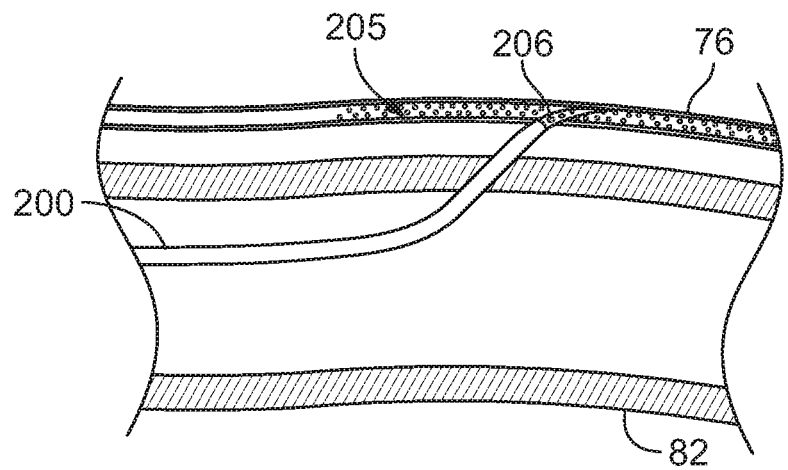
FIG. 6C, FIG. 6D show a catheter delivering energy into (or within) a nerve and smooth muscle, respectively.
Figure 6D:
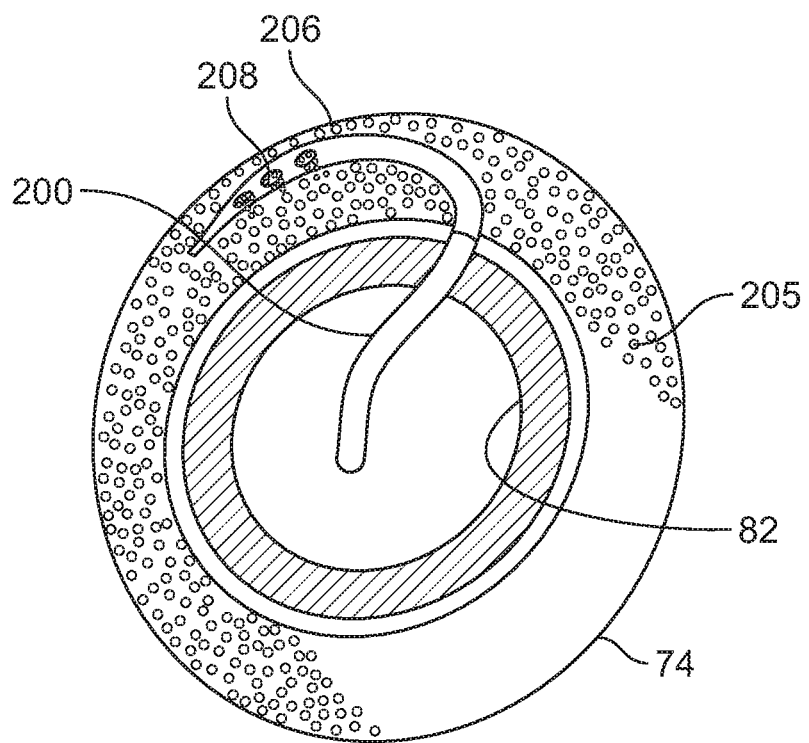

FIG. 6C and FIG. 6D show the catheter 200 delivering energy into (or within) the nerve 76 and smooth muscle 74, respectively. In embodiments, catheter distal section 206 has a needle-like configuration or otherwise sharp tip to penetrate and enter the targeted tissues. The vapor 205 is shown moving, or otherwise flowing through the targeted tissue and follows the boundary of the target tissue because of the presence of higher density cells on the margin or perimeter of the target tissue. The vapor thus moves quickly within the target tissue, and along its boundary, causing thermal ablation as described herein.

In embodiments, a method includes dispersing a vapor through a volume of a first tissue (or filling the first tissue structure with the vapor) with a dose sufficient to render the target tissue non-functional, or to destroy the tissue.

Assessing Catheter Location and Target Contact

In embodiments, as described further herein, methods include assessing the location of the distal end section of the catheter to determine whether the distal section of the catheter is in contact (or otherwise properly located) relative to the target tissue. Nonlimiting examples of target tissue include nerves, smooth muscle, airway tissue, blood vessels as well as tumors, infected or diseased tissues, lymph nodes and tissue growths whether cancerous or benign.

Techniques for confirming or assessing the position of the distal end section may vary. In embodiments, assessing the location of the distal end section may be performed using noninvasive imaging means, and guidance software. Nonlimiting examples of guidance techniques include video or fluoroscopy based tracking and guidance, and electromagnetic based guidance via use of transponders or other sensors or transmitters. Systems may be employed to track the location of the distal end section relative to previously obtained image data of the patient. Examples of tracking and guidance techniques are described in U.S. Pat. No. 7,233,820 to Gilboa; U.S. Pat. No. 7,756,563 to Higgins et al.; U.S. Pat. No. 7,889,905 to Higgins et al.; U.S. Pat. No. 9,265,468 to Rai et al.; and U.S. Patent Publication No. 20160180529 to Rai et al. See, e.g., the Superdimension™ Navigation System, manufactured by Medtronic (Minneapolis, Minn.), and the Archimedes™ System, manufactured by Broncus Medical, Inc., (San Jose, Calif.).

Additionally, in embodiments, the physician can preoperatively plan one or more routes through the airways to the target tissue. An entire pathway or route may be planned from the mouth or nasal passageway, through the airways, and to the target tissue outside of the airway. Then, the pre-planned or pre-determined route may be used during the procedure to guide the physician. One of the above described guidance techniques can be used to assess the location of the catheter as it is advanced into the target position. Once the position of the catheter is confirmed to be at the proper location, the catheter is activated to ablate the targeted tissue. Examples of a route planning techniques are described in U.S. Pat. No. 9,037,215 and U.S. Patent Publication No. 2009/0156895, both to Higgins et al. See also the LungPoint® Planner, manufactured by Broncus Medical, Inc., (San Jose, Calif.).

Additionally, in embodiments, automatic and semi-automatic compiling and evaluation of lung image data, image reconstruction, and display is performed. See, e.g., U.S. Pat. No. 9,037,215 to Higgins et al., and U.S. Patent Publication Nos. 2009/0156895 and 2010/0310146 both to Higgins et al., and 2014/0275952 to Monroe et al. Additionally, assessment of the position of the catheter may be performed via empirical techniques including observing movement of the nerve/airway and/or measuring nerve activity as the catheter tip is moved into and out of contact with the nerve (namely, hitting or probing).

Figure 7:
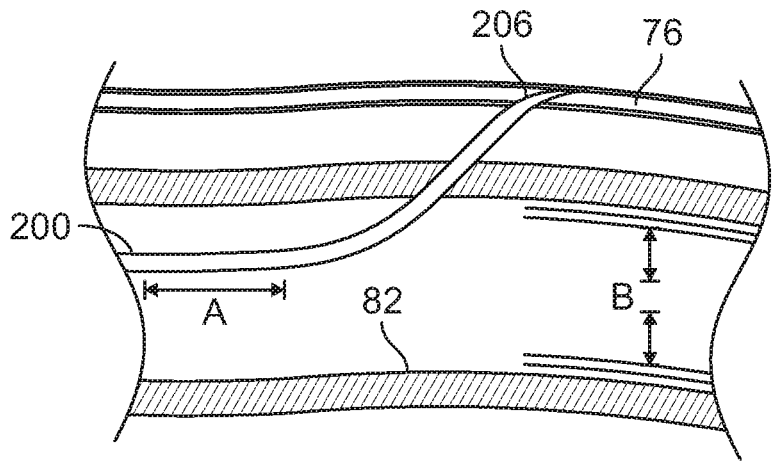
FIG. 7 is an illustration of a vapor ablation catheter being advanced into an extra-airway target tissue, resulting in motion of the airway.

In embodiments, and with reference to FIG. 7, the distal end section 206 of the catheter 200 is shown advanced through an opening in the airway wall 82, and a needle tip inserted into the nerve 76. The physician may visually observe movement (B) of the airway wall in response to advancement (A) of the catheter towards the nerve 76. Airway spasms may be visible by a bronchoscope positioned in the airway. Movement or spasms can be indicative of the tip 206 penetrating or making contact with the nerve.

Additionally, external sensors may interrogate or confirm contact between the distal tip and the nerve or smooth muscle. Such tests record or sense nerve activity or electrical activity in a minimally or noninvasive manner. Nonlimiting examples of external sensors include electromyography (EMG) sensors and systems. In embodiments, a surface-type EMG sensor is affixed to the skin of the patient to monitor nerve activity.

Figure 8:
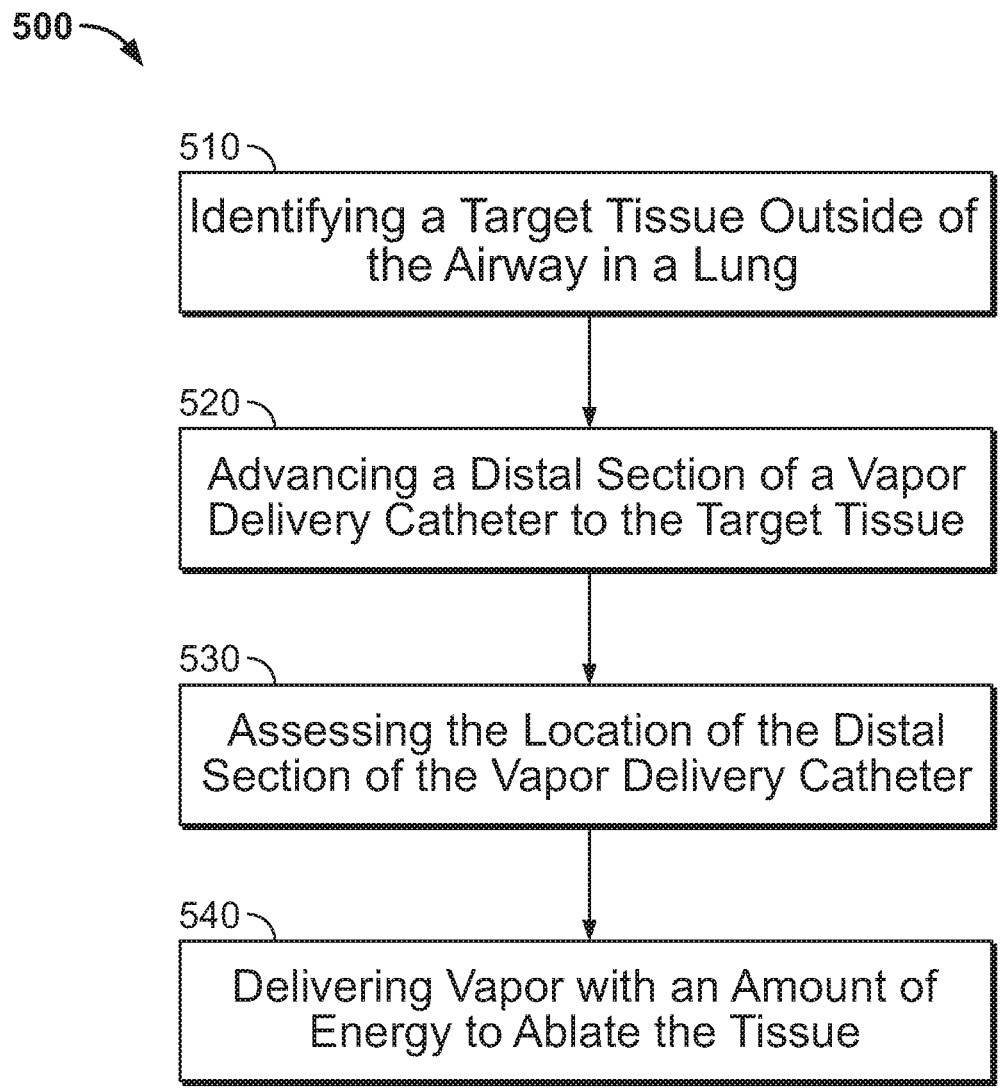
FIG. 8 is a flowchart of a method for treating asthma.

FIG. 8 is a flowchart describing a method for treating asthma 500 in accordance with one embodiment of the invention.

Step 510 states to identify a target tissue outside of the airway in a lung. As described above, examples of target tissue include a nerve and airway smooth muscle. Noninvasive means may be applied to view and identify the target.

Step 520 states to advance a distal section of a vapor delivery catheter to the target tissue. In embodiments, the distal section of the catheter is a sharpened tip which is adapted to penetrate the airway wall, creating an opening through the airway wall. The energy delivery tip is further advanced outside of the airway towards the target tissue. In embodiments, the catheter distal section is advanced into the target tissue, or in contact with the target tissue.

In embodiments, the catheter distal section is curved about, or flush with the nerve, or otherwise manipulated until the egress ports face or are aimed at the nerve tissue.

In other embodiments, the catheter distal section is advanced through a pre-existing opening, passageway, or ancillary appliance or instrument channel. Techniques and instruments for creating passageways and installing working tubes through the airway wall, and for performing procedures through the passageways, are described in, for example, U.S. Pat. Nos. 8,409,167 and 8,709,034.

Step 530 states to assess the location of the distal section of the catheter. Assessing may be performed by determining whether the energy delivery section is in contact with the target tissue to be ablated using a number of different techniques as described herein. In embodiments, confirmation of the location of the distal section of the vapor delivery catheter is performed by probing the target tissue with the catheter and visually observing movement of the tissue structure commanded by the nerve. However, a wide variety of techniques may be employed to assess the location of the vapor delivery catheter.

Step 540 states to deliver vapor with an amount of energy to ablate the tissue. As described herein, the amount and type of energy (flow rate, composition, temperature) may be controlled by the system and based on the characteristics of the tissue such as volume, mass, density, location, and type of tissue. Example quantities or amounts of energy range from 10 to 2000 calories, and in embodiments 100 to 1000 calories. The vapor is delivered from the egress ports into the tissue. The vapor tends to follow the boundary of the airway, raising the temperature uniformly across the target tissue as opposed to developing a large temperature gradient. Ablating the target tissue (e.g., the nerve and/or smooth muscles surrounding the airway) serves to alleviate the conditions associated with asthma as described herein.

In embodiments, the catheter may be moved to additional target locations along the airway, or a different airway and the procedure repeated.

Additionally, in embodiments, the location of the catheter is assessed, and if the catheter is not in proper position, the catheter is further manipulated and the step of assessing is repeated. The process may be repeated until the catheter is ultimately in the desired position.

Lung Cancer Treatment

Figure 9:
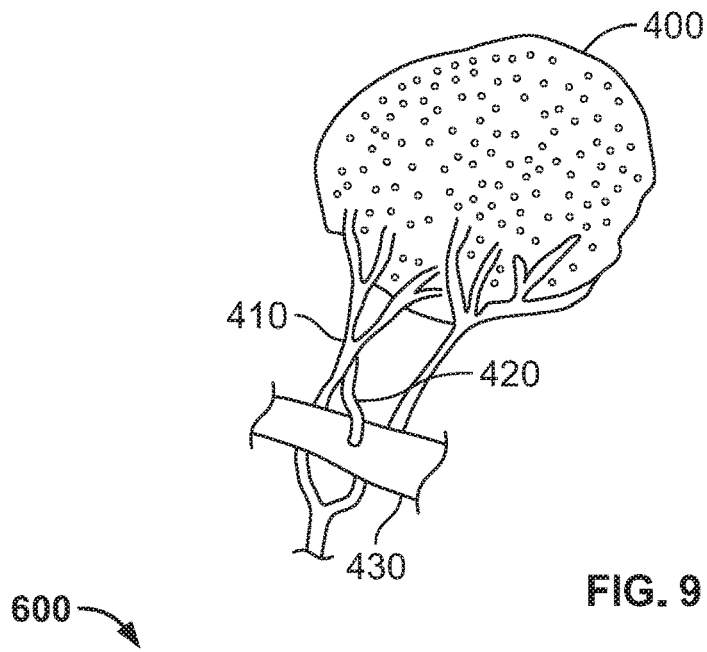
FIG. 9 is an illustration of a vapor ablation catheter advanced into a blood vessel for treating lung cancer.

FIG. 9 illustrates a method for treating a lung tumor 400 in accordance with one embodiment of the invention. At least one blood vessel 410 is shown feeding the tumor 400. A specific blood vessel may be identified prior to the procedure as a candidate target tissue to ablate, thereby cutting off the blood supply to the tumor, and ultimately destroying the tumor. Identifying the blood vessel may be carried out as described above in connection with identifying the target tissues. Image data of a patient may be used to identify targets prior to the procedure. Alternatively, real-time diagnostic means may identify the target tissues including, for example, imaging ultrasound, Doppler, and fluoroscopy.

FIG. 9 also shows a distal section of an energy delivery catheter 420 advanced from the airway 430 to the target blood vessel 410 outside of the airway.

The tip is shown contacting or flush with the surface of the blood vessel. As described above, location of the tip relative to the vessel is assessed or confirmed prior to ablating the tissue. Once the location of the energy delivery section is confirmed, the instrument is activated.

In embodiments, the catheter tip can feature an atraumatic shape, and at least one vent for directing vapor to the blood vessel. The steps of the method may be repeated to ablate several vessels serving to stop all blood flow to the tumor, and causing the tumor to be destroyed. Additionally, by delivering the vapor as described above, heat is applied directly and evenly across the targeted blood vessel, and collateral damage to nearby tissue is avoided.

Figure 10:
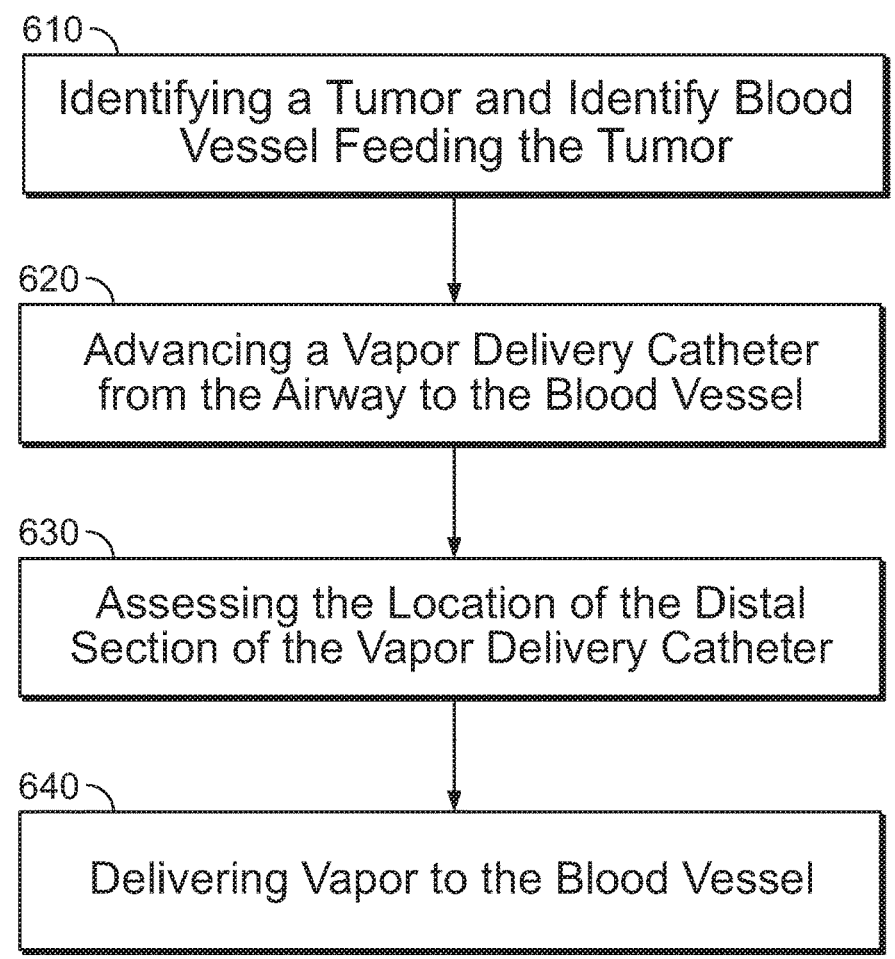
FIG. 10 is a flowchart of a method for treating lung cancer.

FIG. 10 is a flowchart setting forth a method 600 for treating cancer in accordance with an embodiment of the invention.

Step 610 states to identify a tumor and blood vessel feeding the tumor. Identifying the tumor and blood vessel may be performed preoperatively based on image data as described herein.

The tissue structures may be identified in images manually by the physician or the image data may be analyzed semi-automatically by computer systems to identify tissue structures, and present or display candidate structures. Examples of segmentation techniques are described in, for example, US 2010/0310146 to Higgins et al.

Additionally, in embodiments, as described herein, an entire pathway or route may be planned from the mouth or nasal passageway, through the airways, and to the target tissue outside of the airway. Providing a pre-planned route to the extra-airway target helps the physician reach the target.

Step 620 states to advance a vapor delivery catheter from the airway to the blood vessel. As described herein, the distal section of the catheter may be manipulated towards the blood vessel under image guidance.

Step 630 states to assess the location of the catheter to determine whether the apparatus is in position to ablate the tissue. In embodiments, the desired location of the catheter is towards or facing the blood vessel. In embodiments, the desired location of the catheter is in contact with the blood vessel. As described herein, the location of the distal section of the catheter may be assessed using image guidance or other means.

Additionally, tracking or guidance systems as descried herein may be employed to show real-time movement and location information of the catheter. In embodiments, guidance systems indicate the real-time location of the catheter, a path to follow, and a target to aim and move towards. Thus, one may confirm position using the tracking system prior to activating vapor delivery.

Step 640 states to deliver vapor to the feeder blood vessel, leading to the destruction of the tumor. By delivering the vapor as described above, heat is applied directly and evenly across the targeted blood vessel, and collateral damage to nearby tissue is avoided. The process may be repeated to ablate several vessels serving to stop all blood flow to the tumor, causing the tumor to be destroyed.

Other Embodiments

The shape and configuration of the catheter may vary widely. In embodiments, the distal section of the energy delivery catheter includes a discrete surface area, structure, or element from which the energy is sent to the target tissue. In embodiments, the distal section of the energy deliver catheter is in the form of a thin wire.

In embodiments, shape memory materials may be employed to provide a predetermined shape when released from a constrained member.

Additionally, control members such as pull wires may be incorporated into the catheter to adjust the curvature of the distal section such that the distal section may be steered to cover an exterior surface of the nerve and smooth muscle.

Other modifications and variations can be made to the disclosed embodiments without departing from the subject invention. It is intended that features, steps, and components of the above described embodiments may be combined in any way or order except where exclusive of one another.

We claim:

1. A method for treating airway constriction in a lung of a patient, the airway having an airway wall and an exterior surrounded by a target tissue, the method comprising:
   providing a vapor delivery catheter, the vapor delivery catheter comprising a proximal section, an intermediate section, and a distal section comprising at least one egress port and a distal tip;
   advancing the distal section of the vapor delivery catheter along said airway;
   manipulating the distal section of the vapor delivery catheter from a location inside said airway through the airway wall to a position outside of the airway;
   assessing the position of the distal section of the vapor delivery catheter wherein the assessing is performed by hitting the target tissue outside of the airway with the distal tip of the vapor delivery catheter and evaluating constriction movement within the airway responsive to the hitting; and
   delivering vapor into the target tissue from the at least one egress port to ablate the target tissue, wherein the step of delivering is performed by directing the vapor directly at an exposed surface of the target tissue.

2. The method of claim 1, comprising adjusting the position of the distal section of the vapor delivery catheter after the assessing step, and prior to the delivering step.

3. The method of claim 1, wherein the assessing step is also based on a nerve activity monitor.

4. The method of claim 1, wherein the vapor causes heat to be applied directly and uniformly across the target tissue.

5. The method of claim 1, further comprising creating an opening through the airway wall, through which the distal section of the vapor delivery catheter is advanced towards the target tissue.

6. The method of claim 5, wherein the creating is performed with the vapor delivery catheter.

7. The method of claim 1, wherein the target tissue is a nerve responsible for controlling movement of muscles associated with airway motion.

8. The method of claim 1, wherein the distal section of the vapor delivery catheter comprises a face surface in which the at least one egress port is located.

9. The method of claim 8, wherein the face surface is manipulated into said position such that the at least one egress port is aimed towards an exterior surface of the target tissue.

10. The method of claim 1, wherein the distal section of the vapor delivery catheter is a rigid needle having a sharp tip.

11. The method of claim 1, wherein the at least one egress port comprises a plurality of egress ports.

12. The method of claim 1, further comprising creating an opening through the airway wall, through which the distal section of the vapor delivery catheter is advanced towards the target tissue, and installing a tubular appliance in the opening in the airway wall, through which the distal section of the vapor delivery catheter is advanced towards the target tissue.

13. A method for treating airway constriction in a lung of a patient arising from asthma or COPD by ablating a target tissue located on an exterior of the airway, the method comprising:
   providing an elongate energy delivery catheter comprising a proximal section, an intermediate section, and a distal section and a distal tip;
   advancing the distal section of the energy delivery catheter along the airway, through an opening in a wall of the airway, and to a position outside the airway;
   assessing the position of the distal section of the vapor delivery catheter wherein the assessing is performed by moving the distal tip into and out of physical contact with the target tissue outside of the airway and evaluating constriction movement within the airway responsive to the physical contact;
   adjusting said position based on the assessing step, such that energy delivery is aimed towards the target tissue probed in the assessing step; and
   delivering energy to or within the target tissue from the distal section of the energy delivery catheter to ablate the target tissue.

14. The method of claim 13, wherein the energy delivery catheter comprises a working surface or face portion along the distal section, and the working surface or face portion comprises at least one egress port from which the energy is sent to the target tissue.

15. The method of claim 14, wherein the target tissue is a nerve to control smooth muscle.

16. The method of claim 13, wherein the step of delivering energy comprises delivering a vapor.

17. The method of claim 13, wherein the assessing step is also based on imaging.

18. The method of claim 13, wherein the delivering step is carried out by sending vapor along a boundary of the target tissue.

19. The method of claim 13, wherein the airway is second or greater generation airway.

\* \* \* \* \*